United States Patent [19]

Dawson et al.

[11] 4,454,341

[45] Jun. 12, 1984

[54] NAPHTHYL OR TETRAHYDRONAPHTHYL-SUBSTITUTED NAPHTHOIC ACID AND DERIVATIVES

[75] Inventors: Marcia I. Dawson, Los Altos; Peter D. Hobbs, Redwood City; Krzysztof A. Derdzinski, Mountain View, all of Calif.

[73] Assignee: SRI International, Menlo Park, Calif.

[21] Appl. No.: 471,744

[22] Filed: Mar. 3, 1983

[51] Int. Cl.$^3$ .............................................. C07C 69/76
[52] U.S. Cl. ...................... 560/100; 560/56; 562/467; 562/490; 564/172; 564/180; 424/308; 424/317; 424/324
[58] Field of Search ............... 560/100, 56; 562/467, 562/490; 564/172, 180; 424/308, 317, 324

[56] References Cited

U.S. PATENT DOCUMENTS

| 3,821,253 | 6/1974 | Fried et al. | 560/100 |
| 3,896,157 | 7/1975 | Fried et al. | 560/100 |
| 4,326,055 | 4/1982 | Lolliger | 560/100 |
| 4,356,188 | 10/1982 | Pacheco et al. | 560/100 |

OTHER PUBLICATIONS

Boutwell, R. K. et al., Adv. in Enzyme Regulation, vol. 17, Ed. Weber, G. Pergamon Press (1979).
Verma, A. K. et al., Cancer Res. (1979) 39: 419–427.
Verma and Boutwell, Cancer Res. (1979) 37: 2196–2201.
Loeliger, P. et al., Eur. J. Med. Chem.–Chemia Therapeutica (1980) 15: 9–15.

Primary Examiner—Paul J. Killos
Attorney, Agent, or Firm—Ciotti & Murashige

[57] ABSTRACT

Compounds of the formulas:

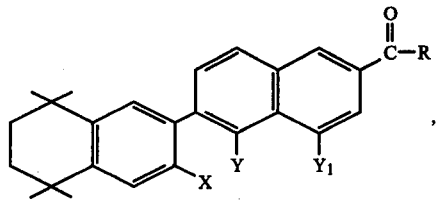

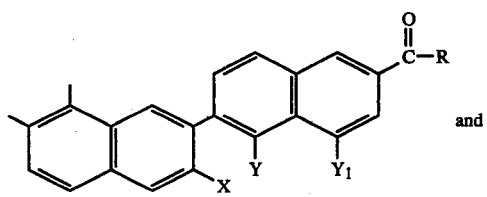

and

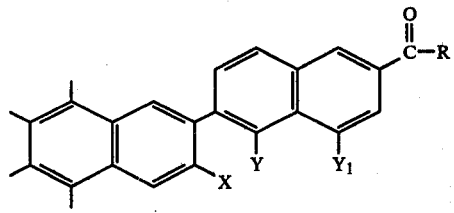

where X is methyl, methoxy, chlorine, or hydrogen, Y and $Y_1$ are fluorine or hydrogen, R is hydroxy, alkoxy with 0 or 1 hydroxy substituent, aroxy, or $NR^1R^2$ where $R^1$ is hydrogen, alkyl with 0 or 1 hydroxy substituent or aryl and $R^2$ is alkyl with 0 or 1 hydroxy substituent or aryl with the proviso that when Y or $Y^1$ is fluorine, the other Y or $Y^1$ is hydrogen. These compounds are useful as chemopreventive agents for inhibiting tumor promotion in epithelial cells and for treating nonmalignant skin disorders.

44 Claims, No Drawings

NAPHTHYL OR TETRAHYDRONAPHTHYL-SUBSTITUTED NAPHTHOIC ACID AND DERIVATIVES

REFERENCE TO GOVERNMENT GRANT OR CONTRACT

The invention described herein was made in the course of work under grants and contract from the National Cancer Institute.

TECHNICAL FIELD

The inventon is in the fields of naphthyl or tetrahydronaphthyl substituted naphthoic acid chemistry and chemotherapy. More particularly the invention relates to certain naphthyl or tetrahydronaphthyl-substituted naphthoic acids and derivatives which are analogues of retinoic acid.

BACKGROUND ART

The progressive loss of the regulation of cellular differentiation by epithelial cells can result in cancer. Retinoic acid and some of its analogues (retinoids) have been investigated as "chemopreventive" agents, that is, agents that interfere with tumor promotion in epithelial cells. Boutwell, R. K., et al, *Advances in Enzyme Regulation* V.17 Ed. Weber, G., Pergamon Press (1979); Verma, A. K., et al, *Cancer Res* (1979) 39:419–427; Dawson, M. I., et al, *J Med Chem* (1981) 24:583–592.

The Dawson, M. I., et al article reports the preparation of (1E,3E)- and (1Z,3E)-1-(4-carboxyphenyl)-2-methyl-4-(2,6,6-trimethyl-1-cyclohexen-1-yl)-1,3-butadiene, the methyl and ethyl esters thereof, (E)-1-(2-carboxyphenyl)4-methyl-6-(2,6,6-trimethyl-1-cyclohexen-1-yl)-1,3,5-hexatriene and the methyl ester thereof, (E)-1-[2-(tetrahydropyranyloxy)phenyl]-4-methyl-6-(2,6,6-trimethyl-1-cyclohexen-1-yl)-1,3,5-hexatriene and the (1E,3Z,5E) isomer thereof. Some of these aromatic retinoic acid analogues exhibited biological activity in the ornithine decarboxylase (ODC) assay, which assay is described by Verma, A. K. and Boutwell, R. K., *Cancer Res* (1979) 37:2196–2201.

In commonly owned copending application Ser. No. 434,622, filed Oct. 15, 1982, the syntheses of two naphthoic retinoids, methyl 6-[2-(2,6,6-trimethyl-1-cyclohexen-1-yl)ethenyl]-2-naphthoate and 6-[2-(2,6,6-trimethyl-1-cyclohexen-1-yl)ethenyl]-2-naphthoic acid, are described. The latter compound also exhibited activity in the ODC assay.

Other reported aromatic retinoic acid analogues with biological activity are 4-[(E)-2-(1,2,3,4-tetrahydro-1,1,4,4-tetramethyl-6-naphthyl)-1-propen-1-yl]benzoic acid and esters and amides thereof. These compounds exhibit a very marked therapeutic effect against carcinogen-induced skin papillomas. Loeliger, P., German Pat. No. 28543546, July 5, 1979; Loeliger, P., et al, *Eur J Med Chemica Therapeutica*, (1980) 15:9–15. The benzoic acid ethyl ester of these analogues also exhibits activity in the ODC assay, Dawson, M. I. unpublished data. However there is a problem in that the double bond in the propenyl moiety of these compounds is relatively unstable.

A principal aspect of this invention is to provide naphthyl or tetrahydronaphthyl substituted naphthoic analogues of retinoic acid which are biologically active, stable and which may exhibit lesser toxicity than other aromatic retinoic acid analogues.

DISCLOSURE OF THE INVENTION

The naphthyl and tetrahydronaphthyl substituted naphthoic acids of the invention are compounds of the formula:

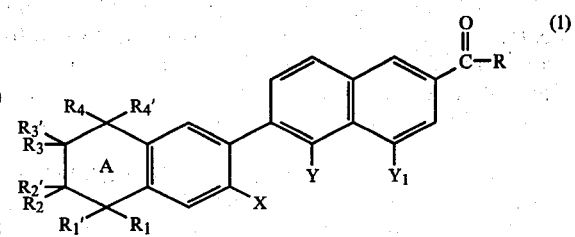

wherein ring A is either a saturated ring and $R_1$, $R_1'$, $R_4$, and $R_4'$ are methyl and $R_2$, $R_2'$, $R_3$, and $R_3'$ are hydrogen or an aromatic ring and $R_3=R_3'=$methyl, $R_4=R_4'=$methyl, $R_2=R_2'=$methyl or hydrogen, and $R_1=R_1'=$methyl or hydrogen, and X is methyl, methoxy, chlorine or hydrogen, Y and $Y_1$ are fluorine or hydrogen, R is hydroxy, alkoxy with 0 or 1 hydroxy substituent, aroxy, or $NR^1R^2$ where $R^1$ is hydrogen, alkyl with 0 or 1 hydroxy substituent, or aryl and $R^2$ is alkyl with 0 or 1 hydroxy or aryl with the provisos that when ring A is unsaturated and $R_1=R_1'=$hydrogen $R_2=R_2'=$hydrogen, when ring A is unsaturated and $R_2=R_2'=$hydrogen $R_1=R_1'=$hydrogen and that when Y or $Y_1$ is fluorine the other Y or $Y_1$ is hydrogen.

When used as pharmaceuticals, eg, as a chemopreventive agent or for treating skin disorders such as proliferative skin diseases or acne, one or more of these retinoids is combined with a suitable pharmaceutically acceptable carrier and an effective dose thereof is administered to the patient.

MODES FOR CARRYING OUT THE INVENTION

The alkoxy groups represented by R will usually contain 1 to about 10 carbon atoms and have 0 or 1 hydroxy substituent, preferably 1 to 4 carbon atoms, and have 0 or 1 hydroxy substituent and the aroxy groups represented thereby will usually be mononuclear and contain 6 to 15 carbon atoms, more usually 6 to 10 carbon atoms and have 0 or 1 hydroxy or alkoxy substituent. Preferred aroxy groups are phenoxy and hydroxy- or $C_1$–$C_4$ alkoxy-monosubstituted phenoxy. The alkoxy groups represented by R may be straight chain or branched chain. Examples of such alkoxy groups are methoxy, ethoxy, n-propoxy, i-propoxy, n-butoxy, s-butoxy, t-butoxy, n-pentoxy, n-hexoxy, 2-methylpentoxy, n-heptoxy, 2-hydroxyethoxy, 3-methylhexoxy, n-octoxy and n-decoxy. Examples of aroxy groups are phenoxy,o-, m-, p-hydroxyphenoxy o-, m-, p-methoxyphenoxy, toloxy, cumoxy, xyloxy, and naphthoxy.

The alkyl groups represented by $R^1$ and $R^2$ may be straight chain or branched chain. They will typically each contain 1 to 8 carbon atoms with 0 or 1 hydroxy substituent, preferably 1 to 4 carbon atoms, and have 0 or 1 hydroxy substituent. Examples of such alkyl groups are methyl, ethyl, propyl, isopropyl, n-butyl, s-butyl, n-amyl, n-hexyl, 2-methylamyl, n-heptyl, 3-methylhexyl, n-octyl, hydroxymethyl, 2-hydroxyethyl, 3-hydroxypropyl, 2-hydroxyhexyl and the like. The corresponding aryl groups represented by $R^1$ and $R^2$ may be substituted or unsubstituted mononuclear or polynuclear moieties. The substituents will usually be lower (ie, 1 to 4 carbon atoms) alkyl, monohydroxyalkyl, lower alkoxy, monohydroxyalkoxy or hydroxy. When substituted, the group will usually be mono-substituted. Examples of such groups are phenyl, o-, m-, or p-hydroxyphenyl, o-, m-, or p-methoxyphenyl, ethylbenzyl, cumyl and the like. These aryl groups will usually contain 6 to about 15 carbon atoms, more usually 6 to 10 carbon atoms. Phenyl, 4-hydroxyphenyl, and 4-methoxyphenyl are preferred aryl groups.

Examples of acids (R=OH) represented by formula (1) are:

6-(1,2,3,4-tetrahydro-1,1,4,4-tetramethyl-6-naphthyl)-2-naphthoic acid
6-(1,2,3,4-tetrahydro-1,1,4,4,7-pentamethyl-6-naphthyl)-2-naphthoic acid
6-(1,2,3,4-tetrahydro-1,1,4,4-tetramethyl-7-methoxy-6-naphthyl)-2-naphthoic acid
6-(1,2,3,4-tetrahydro-1,1,4,4-tetramethyl-7-chloro-6-naphthyl)-2-naphthoic acid
6-(1,2,3,4-tetrahydro-1,1,4,4-tetramethyl-6-naphthyl)-4-fluoro-2-naphthoic acid
6-(1,2,3,4-tetrahydro-1,1,4,4-tetramethyl-6-naphthyl)-5-fluoro-2naphthoic acid
6-(1,2,3,4-tetrahydro-1,1,4,4-tetramethyl-7-methoxy-6-naphthyl)-4-fluoro-2-naphthoic acid
6-(1,2,3,4-tetrahydro-1,1,4,4-tetramethyl-7-chloro-6-naphthyl)-4-fluoro-2-naphthoic acid
6-(1,2,3,4-tetrahydro-1,1,4,4-tetramethyl-7-chloro-6-naphthyl)-5-fluoro-2-naphthoic acid
6-(1,2,3,4-tetrahydro-1,1,4,4,7 pentamethyl-6-naphthyl)-4-fluoro-2-naphthoic acid
6-(1,2,3,4-tetrahydro-1,1,4,4,7 pentamethyl-6-naphthyl)-5-fluoro-2-naphthoic acid
6-(3,4-dimethyl-6-naphthyl)-2-naphthoic acid
6-(3,4,7-trimethyl-6-naphthyl)-2-naphthoic acid
6-(3,4-dimethyl-7-methoxy-6-naphthyl)-2-naphthoic acid
6-(3,4-dimethyl-7-chloro-6-naphthyl)-2-naphthoic acid
6-(3,4-dimethyl-6-naphthyl)-4-fluoro-2-naphthoic acid
6-(3,4-dimethyl-6-naphthyl)-5-fluoro-2-naphthoic acid
6-(3,4-dimethyl-7-methoxy-6-naphthyl)-5-fluoro-2-naphthoic acid
6-(3,4-dimethyl-7-methoxy-6-naphthyl)-4-fluoro-2-naphthoic acid
6-(3,4-dimethyl-7-chloro-6-naphthyl)-4-fluoro-2-naphthoic acid
6-(3,4-dimethyl-7-chloro-6-naphthyl)-5-fluoro-2-naphthoic acid
6-(3,4,7-trimethyl-6-naphthyl)-4-fluoro-2-naphthoic acid
6-(1,2,3,4-tetramethyl-6-naphthyl)-2-naphthoic acid
6-(1,2,3,4,7-pentamethyl-6-naphthyl)-2-naphthoic acid
6-(1,2,3,4-tetramethyl-7-methoxy-6-naphthyl)-2-naphthoic acid
6-(1,2,3,4-tetramethyl-7-chloro-6-naphthyl)-2-naphthoic acid
6-(1,2,3,4-tetramethyl-6-naphthyl)-4-fluoro-2-naphthoic acid
6-(1,2,3,4-tetramethyl-6-naphthyl)-5-fluoro-2-naphthoic acid
6-(1,2,3,4-tetramethyl-7-methoxy-6-naphthyl)-4-fluoro-2-naphthoic acid
6-(1,2,3,4-tetramethyl-7-methoxy-6-naphthyl)-5-fluoro-2-naphthoic acid
6-(1,2,3,4-tetramethyl-7-chloro-6-naphthyl)-4-fluoro-2-naphthoic acid
6-(1,2,3,4-tetramethyl-7-chloro-6-naphthyl)-5-fluoro-2-naphthoic acid
6-(1,2,3,4,7-pentamethyl-6-naphthyl)-4-fluoro-2-naphthoic acid
6-(1,2,3,4,7-pentamethyl-6-naphthyl)-5-fluoro-2-naphthoic acid Examples of esters (R=alkoxy, aroxy) are the methyl, ethyl, isopropyl, propyl, butyl, pentyl, hexyl, heptyl, octyl, nonyl, decyl, hydroxymethyl, 2-hydroxyethyl, 3-hydroxypropyl, phenyl, p-hydroxyphenyl, o-hydroxyphenyl, p-methoxyphenyl, p-isopropylphenyl, tolyl and naphthyl esters of the above acids.

Examples of naphthamides (R=NR$^1$R$^2$) are the N-methyl, N-ethyl, N-isopropyl, N-butyl, N-hexyl, N-octyl, N-hydroxymethyl, N-2-hydroxyethyl, N-3-hydroxypropyl, N,N-dimethyl, N-phenyl, N-p-hydroxyphenyl, N-p-methoxyphenyl and N-p-ethoxyphenyl naphthamides of the above acids.

The compounds of formula (1) where $R_1$, $R_1'$, $R_4$ and $R_4'$ are methyl, $R_2$, $R_2'$, $R_3$, and $R_3'$ are hydrogen, X is hydrogen, methyl or methoxy, Y and $Y_1$ are hydrogen or fluorine, and R is hydroxy or ethoxy are made by the following scheme:

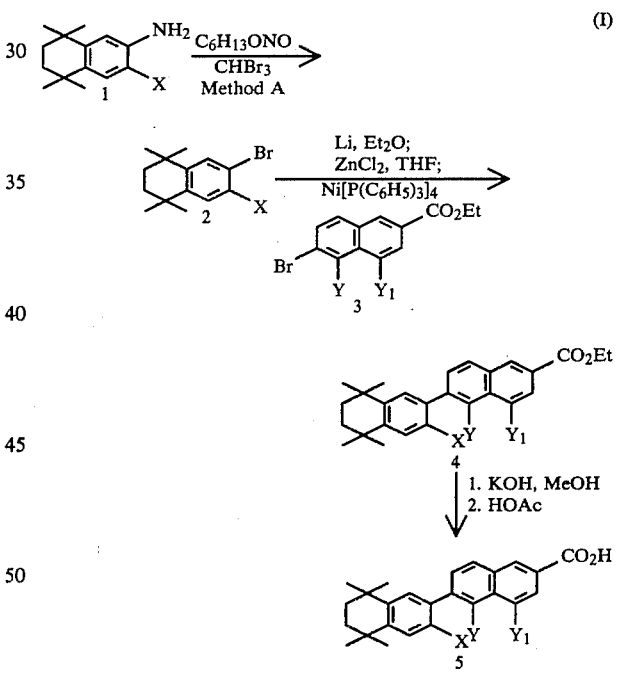

A variation of the above bromination (Method A) using pentyl nitrite instead of hexyl nitrite and also the unsymmetrical aryl coupling step have previously been described. Cadogan, J. I. G., et al, *J. Chem. Soc. C.* (1966) 1249 and Negishi, E., et al, *J. Org. Chem.* (1977) 42:1821, respectively.

6-Bromo-1,2,3,4-tetrahydro-1,1,4,4-tetramethylnaphthalene and 6-bromo-1,2,3,4-tetrahydro-7-methoxy-1,1,4,4 tetramethylnaphthalene (compound 2 in the above scheme where X equals hydrogen or methoxy respectively) may also be prepared by the following method:

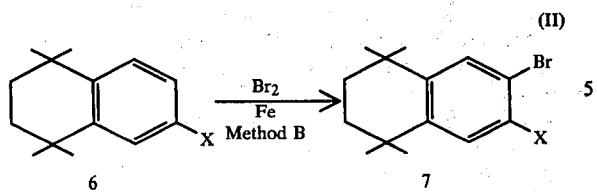

The preferred method for preparing 6-bromo-1,2,3,4-tetrahydro-1,1,4,4-tetramethylnaphthalene, 6-bromo-1,2,3,4-tetrahydro-7-methyl-1,1,4,4-tetramethylnaphthalene and 6-bromo-1,2,3,4-tetrahydro-7-methoxy-1,1,4,4-tetramethylnaphthalene is the following Friedel-Crafts alkylation:

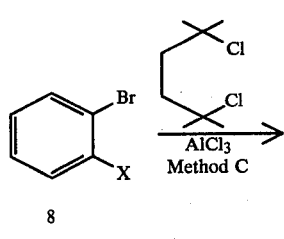

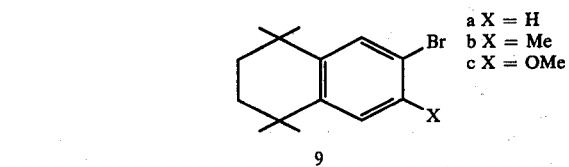

This alkylation (Method C) was first described by Wood, T. F., et al U.S. Pat. No. 3,499,751, Mar. 10, 1970.

The compound 6-bromo-1,2,3,4-tetrahydro-7-chloro-1,1,4,4-tetramethylnaphthalene is made by method A in synthesis (I). However, the coupling step of the two naphthyl moieties (unsymmetrical aryl coupling step) shown in synthesis (I) will not work with this compound. The 7-chloro-tetrahydronaphthyl-substituted naphthalene derivatives however may be prepared by the following route:

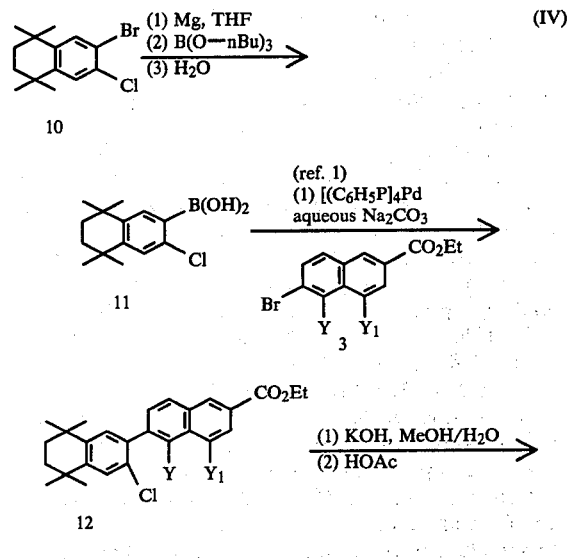

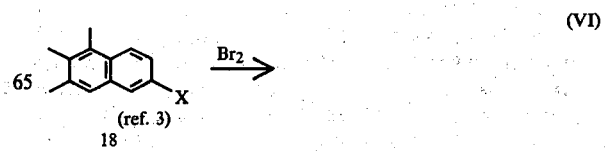

(1) N. Miyaura, T. Yanazi, A. Suzuki, Synthetic Commun (1981) 11:513–519.

6-Bromo-1,2,3,4-tetrahydro-1,1,4,4-tetramethylnaphthalene, 6-bromo-1,2,3,4-tetrahydro-1,1,4,4,7-pentamethylnaphthalene and 6-bromo-1,2,3,4-tetrahydro-7-methoxy-1,1,4,4-tetramethylnaphthalene, (compounds 2 in synthesis (I) and 9a, 9b, and 9c respectively in synthesis (III)) are also transformed to the tetrahydronaphthyl-naphthoic acid ethyl esters by the route shown in synthesis (IV).

The compounds of formula (1) where $R_3$ and $R_4$ are methyl, $R_1$ and $R_2$ are hydrogen, X is hydrogen, methyl, methoxy or chlorine, Y and $Y_1$ are hydrogen or fluorine (with the proviso that when Y is fluorine, $Y_1$ is hydrogen) and R is hydroxy or ethoxy are made by the following scheme:

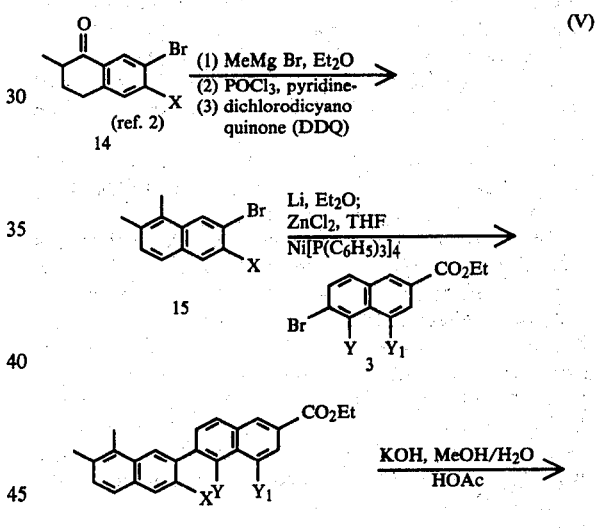

(2) R. R. Smolders, et al, Chimia (1971) 25:59.

The compounds of formula (1) where $R_1$, $R_2$, $R_3$ and $R_4$ are methyl, X is hydrogen, methyl or methoxy, Y and $Y^1$ are hydrogen or fluorine (when Y is fluorine, $Y_1$ is hydrogen) and R is hydroxy or ethoxy are made by the following scheme:

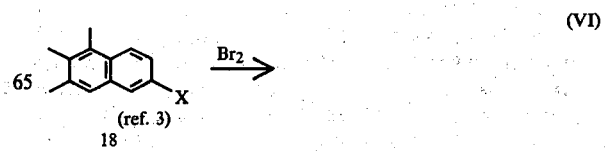

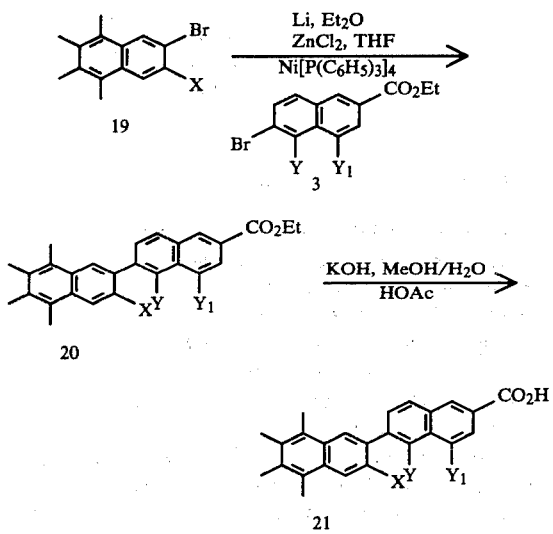

(3) Preparation of 1,2,3,4-tetramethylnaphthalene: M. C. Kloetzel, et al, J Am Chem Soc (1970) 72:273 or W. Herwig, et al, J Am Chem Soc (1959) 81:6203

The other alkyl and aryl esters of the naphthyl and tetrahydronaphthyl-substituted naphthalenes may be made by the transesterification of the ethyl esters.

The alkyl and aryl esters may also be prepared by esterification of the acids or, in some cases, starting with the appropriately derivatized 6-bromo-2-naphthoic acid.

The amides may be made from the acids by conversion to acid chlorides or activated esters followed by reaction with an appropriate amine.

The following examples are provided to further illustrate the compounds and their preparation. They are not intended to limit the invention in any manner.

Abbreviations used in the following example are: Me=methyl; Et=ethyl; Bu=butyl; THF=tetrahydrofuran; LC=high-performance liquid chromatography; IR=infrared; NMR=nuclear magnetic resonance; UV=ultraviolet; DMF=dimethylformamide; GC=gas chromatography; TLC=thin layer chromatography; mp=melting point; bp=boiling point; Ac=$H_3CC(O)$—.

EXAMPLE I

Preparation of 6-(1,2,3,4-Tetrahydro-1,1,4,4-tetramethyl-6-naphthyl)-2-naphthoic acid and Ethyl 6-(1,2,3,4-tetrahydro-1,1,4,4-tetramethyl-6-naphthyl)-2-naphthoate 6-Bromo-1,2,3,4-tetrahydro-1,1,4,4-tetramethylnaphthalene.

Method A. A solution of 0.41 g (2.0 mmol) of 6-amino-1,2,3,4-tetrahydro-1,1,4,4-tetramethylnaphthalene in 1 mL of $CHBr_3$ was added over a period of 30 min to a solution of 0.29 g (2.2 mmol) of n-hexyl nitrite in 6 mL of $CHBr_3$, which was heated in an oil bath at 90°-95° C. $N_2$ was evolved after an induction period of less than 1 min. The solution was dark red at the end of the addition period. The reaction mixture was heated for 1 h more before the $CHBr_3$ and low-boiling material were removed by distillation at 0.3 mm. The brown residue was chromatographed on a 2×30-cm silica gel column with hexane to give 0.34 g of the crude bromide as a white solid. Evaporative distillation (85°-90°/C./0.1 mm) afforded 306 mg (57% yield) of the bromide as a white solid, mp 44.5°-47° C.

Method B. To a stirred 15° C. solution of 4.78 g (25.4 mmol) of 1,2,3,4-tetrahydro-1,1,4,4-tetramethylnaphthalene in 20 mL of $CCl_4$ was added about 10 mg of iron powder followed by the portionwise addition of a 3.33M solution of $Br_2$ $_{L\ in\ CCl_4}$. The addition of $Br_2$ was stopped when GC (0.125-in×6-ft 3% OV-1 column, 120° C., 2 min, 16° C./min to 250° C.) indicated the absence of starting material, $t_R$ 4 min. Approximately 1.15 equivalents of $Br_2$ were required in a period of 1 h to achieve this. The reaction mixture was diluted with ice and saturated $NaHCO_3$ and extracted with hexane (3×30 mL). The extracts were dried ($MgSO_4$) and concentrated at reduced pressure to give 6.5 g of an oil, which was purified by three crystallizations from 6.5 mL of hexane at −80° C. and chromatography on silica gel (0.5% acetone/hexane) to give 3.77 g (56% yield) of white crystals, mp 45°-47° C.; IR (mull) 1590, 1485, 1390, 1365, 1110, 1080, 1065, 870, 840, 810, 750, cm$^{-1}$; $^1H$ NMR ($CDCl_3$) δ 1.25 (s, 12, $CH_3$), 1.66 (s, 4, $(CH_2)_2$), 7.20 (m, 2, 7,8-ArH), 7.39 (broad s, 1, 5-ArH).

Method C. A solution of 3.14 g (20 mmol) of bromobenzene and 1.83 g (10 mmol) of 2,5-dichloro-2,5-dimethylhexane in 30 mL of hexane was cooled to 5° C. while 0.80 g (6 mmol) of anhydrous $AlCl_3$ was added in three portions with vigorous stirring. The reaction mixtures was stirred at 5° to 20° C. for 3 h, at which time TLC (5% acetone/hexane) indicated the disappearance of dichloride. A 5-mL portion of 10% HCl was then added and the reaction mixture was extracted with hexane (3×30 mL). The extracts were washed with 10% HCl and saturated $NaHCO_3$, dried ($MgSO_4$), and concentrated at reduced pressure to give a yellow oil, which was chromatographed on silica gel (0.5% acetone/hexane) to afford 1.84 g (34% yield) of colorless, crystalline bromide. Repeated crystallization from hexane at −80° C. gave 1.38 g of material identical with that produced by method B.

6-Bromo-2-naphthoic acid. A solution of 14.7 (70.9 mmol) of 2-bromonaphthalene and 6.40 g (81.5 mmol) of acetyl chloride in 55 mL of nitrobenzene was added dropwise to a vigorously stirred solution of 10.4 g (78 mmol) of anhydrous $AlCl_3$ in 25 mL of nitrobenzene at 25°-30° C. over a period of 1.3 h. After being stirred for 1 h more at 25° C., the reaction mixture was poured onto 200 g of ice and 30 mL of concentrated HCl. The product was extracted with $Et_2O$ (300, 200, and 100 mL). The extracts were washed with brine and saturated $NaHCO_3$, dried ($MgSO_4$), and concentrated at reduced pressure to afford a brownish oil. Short-path distillation (45°-55° C./25 mm) was used to remove nitrobenzene. The crystalline residue was dissolved in hot hexane (300 ml), filtered, and concentrated at reduced pressure to give 16.3 g (92% yield) of crude 2-acetyl-6-bromonaphthalene. Two crystallizations from hexane afforded 5.3 g (21% yield) of pure product, which had only one spot by TLC (10% EtOAc/hexane) R$_f$ 0.22, mp 99°-101.5° C.; IR (mull) 1670, 1623, 1365, 1355, 1265, 1225, 1175, 880, 820, 800 cm$^{-1}$; $^1H$ NMR ($CDCl_3$) δ 2.71 (s, 3, $CH_3CO$), 7.5-8.2 (m, 4, 3,4,7,8-ArH), 8.03 (s, 1, 5-ArH), 8.44 (s, 1, 1-ArH).

A solution of 6.59 g (26.5 mmol) of 6-acetyl-2-bromonaphthalene in 30 mL of $CHCl_3$ was added gradually over a period of 20 min to 170 mL of a vigorously stirred solution of 5.25% NaOCl in water (Clorox ®) at 65° C. During the addition, $CHCl_3$ distilled off. The temperature of the reaction mixture was then raised to 85° C. for 1 h, at which time TLC (10% EtOAc/hexane) indicated the disappearance of starting material. After cooling, the reaction mixture was poured onto 200 g of ice, and 10.4 g (100 mmol) of NaHSO$_3$ in 40 mL of water was added. The white precipitate was collected by filtration, washed with water, and dried to give 6.44 g (97% yield) of crude acid, which was further purified by washing with 120 mL of boiling 50% EtOAc/hexane, cooling, and filtration to give 5.9 g (93% yield) of white crystals, mp 292°–294° C. (dec). The analytical sample was obtained by crystallization from 50% acetone/C$_6$H$_6$, mp 293°–294° C. (dec); IR (mull) 1684, 1290, 870, 805, 760, 740 cm$^{-1}$; $^1$H NMR (Me$_2$SO-d$_6$) 7.55–8.40 (m, 4, 3,4,7,8-ArH), 8.28 (s, 1, 5-ArH), 8.66 (s, 1, 1-ArH).

Ethyl 6-bromo-2-naphthoate. An ethereal solution of diazoethane was prepared by the portionwise addition over a period of 15 min of 9.65 g (60 mmol) of N-ethyl-N'-nitro-N-nitrosoguanidine to a mixture of 24 mL of 40% aqueous KOH and 150 mL of Et$_2$O at 0° C. with occasional stirring. After cooling to −30° C., the aqueous layer was frozen, and the diazoethane solution in Et$_2$O was decanted for immediate use in the next step.

To a suspension of 5.71 g (22.7 mmol) of 6-bromo-2-naphthoic acid in 200 mL of Et$_2$O, which was cooled to −5° C., was added over a 15-min period the diazoethane solution in 25-mL portions. The mixture was checked by TLC (40% acetone/hexane) for disappearance of acid (R$_f$ 0.16), and then excess diazoethane was destroyed by the addition of HOAc until disappearance of the yellow color of the reaction mixture. Washing with NaHCO$_3$, drying (MgSO$_4$), and concentration at reduced pressure gave 6.5 g of yellowish, crystalline ester, which was purified by crystallization from 60 mL of hexane at −80° C. to give 5.97 g (94% yield) of yellowish flakes, mp 69°–69.5° C.; IR (mull) 1730, 1635, 1275, 1225, 1180, 1135, 1100, 900, 885, 810, 710, 745 cm$^{-1}$; $^1$H NMR (CDCl$_3$) δ1.42 (t, J=7 Hz, 3, CH$_2$CH$_3$), 4.42 (q, J=7 Hz, 2, CH$_2$CH$_3$), 7.45 (dd, J=9 Hz, J=1.8 Hz, 1, 6-ArH), 7.60–7.75 (m, 2, 4, 7-ArH), 7.91 (s, 1, 5-ArH), 7.97 (dd, J=8 Hz, J=1.8 Hz, 3-ArH), 8.46 (s, 1, 1-ArH). Alternatively, heating of 16.0 g of the acid with 200 mL of EtOH, 200 mL of toluene, and 20 mL of concentrated H$_2$SO$_4$ for 14 h with azeotropic removal of H$_2$O afforded 13.0 g of the ester.

Ethyl 6-(1,2,3,4-tetrahydro-1,1,4,4-tetramethyl-6-naphthyl)-2-naphthoate. A solution of 1.344 g (5.03 mmol) of 6-bromo-1,2,3,4-tetrahydro-1,1,4,4-tetramethylnaphthalene in 3 mL of Et$_2$O was added under argon to a stirred mixture of 0.200 g (0.0288 g-at) of Li wire (1% Na) cut in small pieces, which had been prewashed with MeI and hexane, in 2 mL of Et$_2$O at 0° C. The reaction mixture was stirred at 0° C. for 1 h, at which time an aliquot treated with water/hexane showed no aryl bromide by GC analysis (0.125-in×6-ft, 3% OV-1, 120° C., 2 min, 16° C./min to 250° C.). After cooling to −10° C., the supernatant solution of aryllithium reagent was added to a stirred solution of 0.685 g (5.03 mmol) of fused ZnCl$_2$ in 8 mL of THF, which had been precooled to 10° C. After 1 h at 10° C., the resultant arylzinc mixture was added to a stirred solution of 1.116 g (4.00 mmol) of ethyl 6-bromo-2-naphthoate and 0.28 g (0.25 mmol) of tetrakis(triphenylphosphine)nickel(0) in 16 mL of THF at 5° C. The dark reaction mixture was allowed to warm to 20° C. and maintained there for 1 h. It was then poured into 20 mL of cold 10% HCl and extracted with Et$_2$O. Washing with saturated NaHCO$_3$ and brine, drying (MgSO$_4$), and concentration at reduced pressure afforded a crystalline residue, which was recrystallized from hexane at 80° C. to give 0.996 g of white crystals. Impurities were removed by chromatography on silica gel with 0.5% acetone/hexane and recrystallization from Et$_2$O at −20° C. to give 0.645 g (42% yield) of shiny, colorless plates, mp 155.5°–156.5° C.; TLC (10% acetone/hexane) R$_f$ 0.68; LC (Radialpak B, 1% EtOAc/hexane, 2 mL/min, 280 nm) 2.4 min (100%); LC (Radialpak A, MeCN, 2 mL/min, 280 nm) 5.4 min (100%); IR (mull) 1630, 1365, 1280, 1255, 920, 890, 815, 770, 750, cm$^{-1}$; $^1$H NMR (CDDl$_3$) δ 1.33 and 1.37 (2 s, 12, C(CH$_3$)$_2$), 1.45 (t, J=7 Hz, 3, CH$_2$CH$_3$), 1.73 (s, 4, (CH$_2$)$_2$), 4.44 (q, J=7 Hz, 2, CH$_2$CH$_3$), 7.45 (m, 2, 7,8-ArH), 7.65 (broad s, 1, 5-ArH), 7.65–8.18 (m, 5, 3,4,5,7,8-NapH), 8.61 (broad s, 1, 1-NapH).

6-(1,2,3,4-Tetrahydro-1,1,4,4-tetramethyl-6-naphthyl)-2-naphthoic acid. A suspension of 0.434 g (1.12 mmol) of ethyl 6-(1,2,3,4-tetrahydro-1,1,4,4-tetramethyl-6-naphthyl)-2-naphthoate in a solution of 0.628 g (9.5 mmol) of 85% KOH in 1.1 mL of water and 10 mL of EtOH was heated at reflux for 10 min, at which time solution was achieved and TLC (40% acetone/hexane) showed no starting material (R$_f$ 0.90). The reaction mixture was diluted with 20 mL of cold water and acidified with HOAc. The precipitated product was extracted into Et$_2$O (2×100 mL). The extracts were washed with brine, dried (MgSO$_4$), and concentrated at reduced pressure to give 0.396 g of white crystalline product. Recrystallization from 45 mL of acetone at −20° C. afforded 0.309 g (77% yield) of acid as colorless crystals, mp 287.5°–288.5° C.; LC (Radialpak A, 60% MeOH/water, 2 mL/min, 260 nm) 15.1 min (100%); IR (mull) 1680, 1630, 1300, 1220, 910, 880, 810, 770, 740 cm$^{-1}$; $^1$H NMR (Me$_2$SO-d$_6$) 1.28 and 1.35 (2 s, 12, C(CH$_3$)$_2$), 1.68 (s, 4, (CH$_2$)$_2$), 7.46 (m, 2, 7, 8-ArH), 7.73 (s, 1, 5-ArH), 7.8–8.2 (m, 4, 3,4,7,8-NapH), 8.23 (s, 1,5-NapH), 8.63 (2, 1, 1-NapH).

The retinoids of formula (1) may be used topically or systemically as chemopreventive agents and in the treatment, amelioration, or prevention of skin, rheumatic and other disorders for which retinoic acid and other retinoids are useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (nonmalignant conditions of the skin that are characterized by epidermal cell proliferation or incomplete cell differentiation) such as acne, psoriasis, eczema, atopic dermatitis, nonspecific dermatitis and the like. When used for such treatments they will usually be formulated with a pharmaceutical liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to, the dosage form, mode of administration, the condition being treated and particulars of the patient being treated. They will, of course, be administered in chemopreventive (tumor promotion inhibiting) amounts or therapeutically effective amounts. For adult humans such chemopreventive amounts will usually be about 0.01 mg to 10.0 mg daily given in one or more doses. Oral doses will generally be more than topical doses and doses for treating skin disorders will typically be less than doses administered for cancer chemoprevention. The dose for treating skin disorders will be on the order of, but normally less than, the dose of retinoic acid prescribed for the disorder.

The usefulness of the invention compounds was demonstrated by testing the compound of the Example in the ornithine decarboxylase (ODC) assay, Verma, A. K. and Boutwell, R. K., *Cancer Res* (1977) 37:2196–2201, and the tracheal organ culture assay, Newton, D. L.; Henderson, W. R.; and Sporn, M. B., *Cancer Res* (1980) 40:3413–3425. The ODC assay measures a compound's ability to prevent the induction of ODC. The tracheal organ culture assay measures a compound's ability to reverse keratinization.

The ODC assay is carried out as follows. Female Charles River CD-1 mice from Charles River Breeding Laboratories, Wilmington, Mass., are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 µg, 17 nmol) in 0.2 mL of acetone is applied topically to the back of each mouse. The test compound, at one of three dose levels (1.7, 17 and 170 nmol), dissolved in 0.2 mL of acetone is applied 1 hour before the TPA treatment to the test groups; the control group is treated with acetone alone. The mice are killed by cervical dislocations five hours after TPA treatment. Determinations are done in triplicate.

The epidermis is obtained from the sacrificed animals. To obtain sufficient material, the dorsal skins from 2 to 3 mice in each treatment group are pooled. The depilatory agent Nudit® (Helena Rubinstein, N.Y.) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at least another 30 seconds. The skin is placed epidermis side up on a cold plate, and the epidermis is scraped off with a razor blade. The pooled epidermal sheets are homogenized (Polytron PT-10 homogenizer) at 0° to 4° C. for 15–20 seconds in 50 mM sodium phosphate and 0.1 mM ethylenediaminetetraacetic acid (EDTA), at a volume of 1 mL/skin.

The supernatant fraction remaining after centrifugation of the homogenate at $10,000 \times g$ for 30 seconds at 0° C. is used for the enzyme assay. Enzyme activity is determined using the microassay for ODC as described by Verma and Boutwell to measure the release of $^{14}CO_2$ from DL-$[1-^{14}C]$-ornithine (58 mCi/mmol) after incubation with the $10,000 \times g$ supernatant. The incubations are carried out by decanting, with a Pasteur pipette, 100 µL of the supernatant containing 100 to 120 µg of protein into two or three 15-mL Corex tubes in a shaking water bath at 37° C. The assay mixture in the tubes consists of 50 µL of 100 mM sodium phosphate buffer (pH 7.2), 10 µL of 4 mM pyridoxal phosphate, 40 µL of 25 mM dithiothreitol, and 1 µL of 0.1 M EDTA. The center wells in the tubes are filled with 200 µL of a 2:1 solution (v/v) of ethanolamine:2-methoxyethanol. The reaction is started by adding 50 µL of substrate (0.5 µCi of DL-$[1-^{14}C]$-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0.1 µg/ml; hydrocortisone hemisuccinate, 0.1 µg/ml; glutamine, 2 mM; penicillin, 100 units/ml; and streptomycin, 100 µg/ml, added). Cultures are gassed with 50% oxygen, 45% nitrogen, and 5% $CO_2$. The culture dishes are rocked at 35.5–36.0 degrees to allow the tracheas contact with both gas and medium. All tracheas are grown in medium containing no retinoid for the first 3 days. At the end of 3 days, some tracheas are harvested; almost all of these tracheas have significant squamous metaplasia, and approximately 60% have keratinized lesions. The remaining tracheas are then divided into different groups which are treated with either: (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that received no retinoid for the entire 10 day culture period. Retinoids are scored as "inactive" if both keratin and keratohyaline granules are seen; they are scored as "active" if neither keratin nor keratohyaline granules are seen, or if keratohyaline granules alone are absent.

The table below gives the results of these tests.

| Test Compounds | Reversal of Keratinization in Hamster Tracheal Organ Culture | | Inhibition of Induction of Ornithine Decarboxylase by 12-O—Tetradecanoylphorbol-13-acetate in Mouse Skin | |
|---|---|---|---|---|
| | Conc (M) | Active/Total Cultures (%) | Dose (nmol) | % Inhibition of Control |
| Retinoic Acid | $10^{-8}$ | 236/236 (100) | 17 | 87–91 |
| | $10^{-9}$ | 419/474 (88) | | |
| | $10^{-10}$ | 134/256 (52) | | |
| Ethyl 4-[(E)-2-(1,2,3,4-tetrahydro-1,1,4,4-tetra-methyl-6-naphthyl)-1-propen-1-yl]benzoate | | | 17 | 86 |
| | | | 1.7 | 86 |
| 6-(1,2,3,4-Tetra-hydro-1,1,4,4-tetramethyl-6-naphthyl)-2-naphthoic acid | $10^{-9}$ | 7/7 (100) | 17 | 80 |
| | $10^{-10}$ | 7/7 (100) | 1.7 | 56 |
| | $10^{-11}$ | 5/7 (71) | | |
| Ethyl 6-(1,2,3,4-tetrahydro-1,1,4,4-tetramethyl-6-naphtyl)-2-naphthoate | | | 17 | 75 |
| | | | 1.7 | 50 |

These results indicate that the naphthalenic retinoic acid analogues of the invention possess biological activity that makes them useful as chemopreventive agents and therapeutic agents for treating nonmalignant skin disorders. Also because of the difference in structure and other chemical characteristics these retinoids may be less toxic than retinoic acid or its other aromatic analogues. They are also less oxygen and light sensitive than retinoic acid.

Modifications of the above described modes for carrying out the invention that are obvious to those of skill in the fields of organic chemistry, pharmaceuticals, and/or medicine are intended to be within the scope of the following claims.

We claim:

1. A compound of the formula:

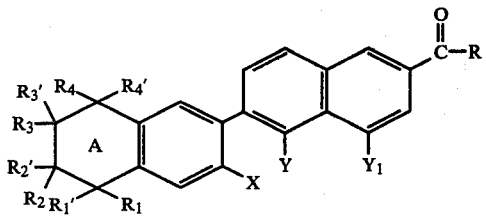

wherein ring A is a saturated ring and $R_1$, $R_1'$, $R_4$, and $R_4'$ are methyl and $R_2$, $R_2'$, $R_3$ and $R_3'$ are hydrogen or an aromatic ring and $R_3=R_3'=$methyl, $R_4=R_4'=$methyl, $R_2=R_2'=$methyl or hydrogen, and $R_1=R_1'=$methyl or hydrogen, and X is methyl, methoxy, chlorine or hydrogen, Y and $Y_1$ are fluorine or hydrogen, R is hydroxy, alkoxy with 0 or 1 hydroxy substituent, aroxy, or $NR^1R^2$ where $R^1$ is hydrogen, alkyl with 0 or 1 hydroxy substituent or aryl and $R^2$ is alkyl with 0 or 1 hydroxy or aryl with the provisos that when ring A is unsaturated and $R_1=R_1'=$hydrogen $R_2=R_2'=$hydrogen, when ring A is unsaturated and $R_2=R_2'=$hydrogen $R_1=R_1'=$hydrogen and that when Y or $Y_1$ is fluorine the other Y or $Y_1$ is hydrogen.

2. A compound of claim 1 wherein the alkoxy represented by R contains 1 to about 10 carbon atoms with 0 or 1 hydroxy substituent, the aroxy group represented by R contains 6 to about 15 carbon atoms, the alkyl groups represented by $R^1$ and $R^2$ each contain 1 to about 8 carbon atoms with 0 or 1 hydroxy substituent and the aryl groups represented by $R^1$ and $R^2$ each contain 6 to about 15 carbon atoms.

3. The compound of claim 1 wherein the alkoxy group represented by R contains 1 to 4 carbon atoms and have 0 or 1 hydroxy substituent, the aroxy group represented by R is phenoxy, monohydoxyphenoxy, or monoalkoxyphenoxy where the alkoxy group contains 1 to 4 carbons atoms, with 0 or 1 hydroxy substituent, the alkyl groups represented by $R^1$ and $R^2$ each contain 1 to 4 carbon atoms and have 0 or 1 hydroxy substituent and the aryl groups represented by $R^1$ and $R^2$ are phenyl, 4-hydroxyphenyl, or 4-methoxyphenyl.

4. A compound of the formula:

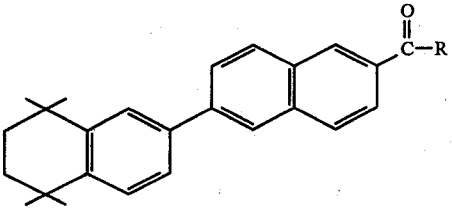

where R is hydroxy or ethoxy.

5. A compound of the formula

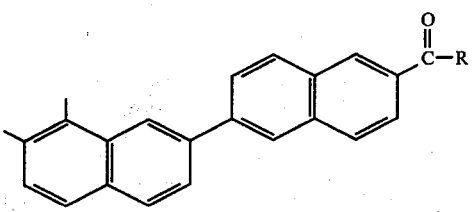

where R is hydroxy or ethoxy.

6. A compound of the formula:

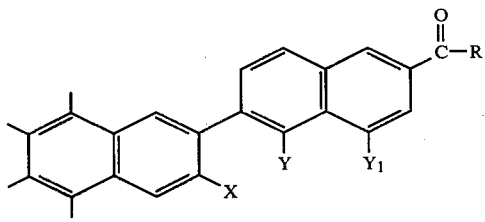

where R is hydroxy or ethoxy.

7. A compound of the formula:

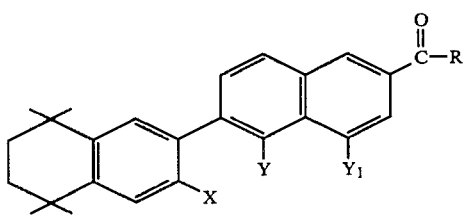

where
(a) X is hydrogen, methyl, methoxy or chlorine, Y is hydrogen, $Y_1$ is fluorine, and R is ethoxy; or
(b) X is hydrogen, methyl, methoxy or chlorine, Y is fluorine, $Y_1$ is hydrogen and R is ethoxy; or
(c) X is hydrogen, methyl, methoxy or chlorine, Y is hydrogen, $Y_1$ is fluorine and R is hydroxy; or
(d) X is hydrogen, methyl, methoxy or chlorine, Y is fluorine, $Y_1$ is hydrogen, and R is hydroxy; or
(e) X is methyl, methoxy or chlorine, Y is hydrogen, $Y_1$ is hydrogen, and R is ethoxy; or
(f) X is methyl, methoxy or chlorine, Y is hydrogen, $Y_1$ is hydrogen and R is hydroxy.

8. A pharmaceutical composition comprising a pharmaceutically effective amount of the compound of claim 1 combined with a pharmaceutically acceptable carrier.

9. A pharmaceutical composition comprising a pharmaceutically effective amount of the compound of claim 2 combined with a pharmaceutically acceptable carrier.

10. A pharmaceutical composition comprising a pharmaceutically effective amount of the compound of claim 3 combined with a pharmaceutically acceptable carrier.

11. A pharmaceutical composition comprising a pharmaceutically effective amount of the compound of claim 4 combined with a pharmaceutically acceptable carrier.

12. A pharmaceutical composition comprising a pharmaceutically effective amount of the compound of claim 5 combined with a pharmaceutically acceptable carrier.

13. A pharmaceutical composition comprising a pharmaceutically effective amount of the compound of claim 6 combined with a pharmaceutically acceptable carrier.

14. A pharmaceutical composition comprising a pharmaceutically effective amount of the compound of claim 7 combined with a pharmaceutically acceptable carrier.

15. A pharmaceutical composition comprising a pharmaceutically effective amount of the compound of claim 8 combined with a pharmaceutically acceptable carrier.

16. A chemopreventive composition for inhibiting tumor promotion in epithelial cells in a living animal comprising a tumor promotion inhibiting amount of the compound of claim 1 combined with a pharmaceutically acceptable carrier.

17. A chemopreventive composition for inhibiting tumor promotion in epithelial cells in a living animal comprising a tumor promotion inhibiting amount of the compound of claim 2 combined with a pharmaceutically acceptable carrier.

18. A chemopreventive composition for inhibiting tumor promotion in epithelial cells in a living animal comprising a tumor promotion inhibiting amount of the compound of claim 3 combined with a pharmaceutically acceptable carrier.

19. A chemopreventive composition for inhibiting tumor promotion in epithelial cells in a living animal comprising a tumor promotion inhibiting amount of the compound of claim 4 combined with a pharmaceutically acceptable carrier.

20. A chemopreventive composition for inhibiting tumor promotion in epithelial cells in a living animal comprising a tumor promotion inhibiting amount of the compound of claim 5 combined with a pharmaceutically acceptable carrier.

21. A chemopreventive composition for inhibiting tumor promotion in epithelial cells in a living animal comprising a tumor promotion inhibiting amount of the compound of claim 6 combined with a pharmaceutically acceptable carrier.

22. A chemopreventive composition for inhibiting tumor promotion in epithelial cells in a living animal comprising a tumor promotion inhibiting amount of the compound of claim 7 combined with a pharmaceutically acceptable carrier.

23. A chemopreventive composition for inhibiting tumor promotion in epithelial cells in a living animal comprising a tumor promotion inhibiting amount of the compound of claim 8 combined with a pharmaceutically acceptable carrier.

24. A therapeutic composition for treating a non-malignant skin disorder comprising a therapeutically effective amount of the compound of claim 1 combined with a pharmaceutically acceptable carrier.

25. A therapeutic composition for treating a non-malignant skin disorder comprising a therapeutically effective amount of the compound of claim 2 combined with a pharmaceutically acceptable carrier.

26. A therapeutic composition for treating a non-malignant skin disorder comprising a therapeutically effective amount of the compound of claim 3 combined with a pharmaceutically acceptable carrier.

27. A therapeutic composition for treating a non-malignant skin disorder comprising a therapeutically effective amount of the compound of claim 4 combined with a pharmaceutically acceptable carrier.

28. A therapeutic composition for treating a non-malignant skin disorder comprising a therapeutically effective amount of the compound of claim 5 combined with a pharmaceutically acceptable carrier.

29. A method of inhibiting tumor promotion in epithelial cells of a human or other living animal patient comprising administering a tumor promotion inhibiting amount of the compound of claim 1 to the patient.

30. A method of inhibiting tumor promotion in epithelial cells of a human or other living animal patient comprising administering a tumor promotion inhibiting amount of the compound of claim 2 to the patient.

31. A method of inhibiting tumor promotion in epithelial cells of a human or other living animal patient comprising administering a tumor promotion inhibiting amount of the compound of claim 3 to the patient.

32. A method of inhibiting tumor promotion in epithelial cells of a human or other living animal patient comprising administering a tumor promotion inhibiting amount of the compound of claim 4 to the patient.

33. A method of inhibiting tumor promotion in epithelial cells of a human or other living animal patient comprising administering a tumor promotion inhibiting amount of the compound of claim 5 to the patient.

34. A method of inhibiting tumor promotion in epithelial cells of a human or other living animal patient comprising administering a tumor promotion inhibiting amount of the compound of claim 6 to the patient.

35. A method of inhibiting tumor promotion in epithelial cells of a human or other living animal patient comprising administering a tumor promotion inhibiting amount of the compound of claim 7 to the patient.

36. A method of inhibiting tumor promotion in epithelial cells of a human or other living animal patient comprising administering a tumor promotion inhibiting amount of the compound of claim 8 to the patient.

37. A method for treating a human or other living animal patient for a nonmalignant skin disorder comprising administering a therapeutically effective amount of the compound of claim 1 to the patient.

38. A method for treating a human or other living animal patient for a nonmalignant skin disorder comprising administering a therapeutically effective amount of the compound of claim 2 to the patient.

39. A method for treating a human or other living animal patient for a nonmalignant skin disorder comprising administering a therapeutically effective amount of the compound of claim 3 to the patient.

40. A method for treating a human or other living animal patient for a nonmalignant skin disorder comprising administering a therapeutically effective amount of the compound of claim 4 to the patient.

41. A method for treating a human or other living animal patient for a nonmalignant skin disorder comprising administering a therapeutically effective amount of the compound of claim 5 to the patient.

42. A method for treating a human or other living animal patient for a nonmalignant skin disorder comprising administering a therapeutically effective amount of the compound of claim 6 to the patient.

43. A method for treating a human or other living animal patient for a nonmalignant skin disorder comprising administering a therapeutically effective amount of the compound of claim 7 to the patient.

44. A method for treating a human or other living animal patient for a nonmalignant skin disorder comprising administering a therapeutically effective amount of the compound of claim 8 to the patient.

* * * * *